(12) United States Patent
Yoshimine

(10) Patent No.: US 10,905,455 B2
(45) Date of Patent: Feb. 2, 2021

(54) ULTRASONIC PROBE

(71) Applicant: OLYMPUS CORPORATION, Hachioji (JP)

(72) Inventor: Hideto Yoshimine, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 317 days.

(21) Appl. No.: 15/876,836

(22) Filed: Jan. 22, 2018

(65) Prior Publication Data
US 2018/0140275 A1 May 24, 2018

Related U.S. Application Data

(63) Continuation of application No. PCT/JP2016/053247, filed on Feb. 3, 2016.
(Continued)

(51) Int. Cl.
A61B 17/32 (2006.01)
A61B 18/00 (2006.01)
A61B 17/16 (2006.01)
A61N 7/02 (2006.01)
A61B 8/08 (2006.01)
(Continued)

(52) U.S. Cl.
CPC .... *A61B 17/320068* (2013.01); *A61B 8/0875* (2013.01); *A61B 8/4444* (2013.01); *A61B 17/1675* (2013.01); *A61B 18/00* (2013.01); *A61N 7/02* (2013.01); *A61B 8/12* (2013.01); *A61B 8/4483* (2013.01); *A61B 2017/00738* (2013.01); *A61B 2017/32007* (2017.08); *A61B 2017/320008* (2013.01); *A61B 2017/320072* (2013.01); *A61B 2017/320073* (2017.08);
(Continued)

(58) Field of Classification Search
CPC .............................................. A61B 17/320068
See application file for complete search history.

(56) References Cited

U.S. PATENT DOCUMENTS 5,211,625 A 5/1993 Sakurai et al.
6,283,981 B1 9/2001 Beaupre
(Continued)

FOREIGN PATENT DOCUMENTS

CN 102843979 A 12/2012
CN 102843982 A 12/2012
(Continued)

OTHER PUBLICATIONS

May 14, 2019 Office Action issued in U.S. Appl. No. 15/674,153.
(Continued)

*Primary Examiner* — Rochelle D Turchen
(74) *Attorney, Agent, or Firm* — Oliff PLC

(57) ABSTRACT

An ultrasonic probe includes a first bent extending portion provided on a distal side with respect to a narrowed portion and extending in such a state as to bend toward a first crossing direction side crossing a longitudinal axis, and a second bent extending portion continuous with the distal side of the first bent extending portion and extending in such a state as to bend toward second crossing direction side opposite to the first crossing direction. The second bent extending portion includes a blade portion, and in a projection seen from the distal side, the first bent extending portion and the second bent extending portion are located within a minimum inside diameter of a sheath.

14 Claims, 11 Drawing Sheets

Related U.S. Application Data

(60) Provisional application No. 62/196,158, filed on Jul. 23, 2015.

(51) Int. Cl.
  *A61B 8/00* (2006.01)
  *A61B 17/00* (2006.01)
  *A61B 8/12* (2006.01)

(52) U.S. Cl.
  CPC ............ *A61B 2017/320084* (2013.01); *A61B 2217/005* (2013.01)

(56) References Cited

U.S. PATENT DOCUMENTS

| | | | |
|---|---|---|---|
| 2002/0077550 | A1 | 6/2002 | Rabiner et al. |
| 2003/0009190 | A1 | 1/2003 | Kletschka et al. |
| 2004/0147945 | A1 | 7/2004 | Fritzsch |
| 2005/0245823 | A1 | 11/2005 | Tsuchiya et al. |
| 2009/0270891 | A1 | 10/2009 | Beaupre |
| 2010/0191173 | A1 | 7/2010 | Kimura et al. |
| 2011/0196398 | A1 | 8/2011 | Robertson et al. |
| 2011/0196399 | A1 | 8/2011 | Robertson et al. |
| 2011/0196400 | A1 | 8/2011 | Robertson et al. |
| 2011/0196403 | A1 | 8/2011 | Robertson et al. |
| 2012/0109191 | A1* | 5/2012 | Marano, Jr. ....... A61B 17/12031 606/213 |
| 2012/0116222 | A1 | 5/2012 | Sawada et al. |
| 2013/0231527 | A1 | 9/2013 | Mirza et al. |
| 2013/0231528 | A1 | 9/2013 | Voic |
| 2014/0066962 | A1 | 3/2014 | Robertson et al. |
| 2015/0230697 | A1* | 8/2015 | Phee ................. A61B 1/00135 600/106 |
| 2015/0272781 | A1* | 10/2015 | Vezzu ................ A61F 9/00745 606/169 |
| 2016/0128711 | A1 | 5/2016 | Cao et al. |
| 2016/0135835 | A1 | 5/2016 | Onuma |
| 2017/0027753 | A1* | 2/2017 | de Santis ............ A61F 9/00763 |
| 2017/0128122 | A1* | 5/2017 | Rontal ............... A61B 18/1206 |
| 2017/0143398 | A1 | 5/2017 | Young et al. |
| 2018/0000505 | A1 | 1/2018 | Onuma et al. |

FOREIGN PATENT DOCUMENTS

| | | |
|---|---|---|
| CN | 103654950 A | 3/2014 |
| EP | 0 968 684 A1 | 1/2000 |
| EP | 1591071 A1 | 11/2005 |
| EP | 3025659 A1 | 6/2016 |
| EP | 3243463 A1 | 11/2017 |
| EP | 3260064 A1 | 12/2017 |
| JP | S48-15110 B1 | 5/1973 |
| JP | S62-172393 A | 7/1987 |
| JP | S62-268549 A | 11/1987 |
| JP | H01-75416 U | 5/1989 |
| JP | H07-059789 A | 3/1995 |
| JP | H9-327466 A | 12/1997 |
| JP | 2000-254136 A | 9/2000 |
| JP | 2003-116870 A | 4/2003 |
| JP | 2005-152098 A | 6/2005 |
| JP | 2005-516663 A | 6/2005 |
| JP | 2005-312675 A | 11/2005 |
| JP | 2012-192072 A | 10/2012 |
| JP | 2013-519437 A | 5/2013 |
| JP | 2013-519438 A | 5/2013 |
| JP | 2013-519441 A | 5/2013 |
| JP | 2015-510787 A | 4/2015 |
| WO | 2009/88390 A1 | 7/2009 |
| WO | 2010/087060 A1 | 8/2010 |
| WO | 2011/158792 A1 | 12/2011 |
| WO | 2012/061646 A1 | 5/2012 |
| WO | 2015/010505 A1 | 1/2015 |
| WO | 2015/045198 A1 | 4/2015 |
| WO | 2015/046349 A1 | 4/2015 |

OTHER PUBLICATIONS

Jan. 28, 2019 Office Action issued in Chinese Patent Application No. 201580075895.8.
Jan. 29, 2019 Office Action issued in Chinese Patent Application No. 201680009794.5.
Nov. 11, 2019 Office Action issued in Chinese Patent Application No. 201680043367.9.
May 29, 2019 Office Action issued in U.S. Appl. No. 15/673,682.
Nov. 29, 2019 Office Action issued in Chinese Patent Application No. 201580081886.X.
Oct. 25, 2019 Office Action issued in U.S. Appl. No. 15/673,682.
Aug. 3, 2018 extended Search Report issued in European Patent Application No. 15898971.5.
Aug. 22, 2019 Office Action issued in Chinese Patent Application No. 201580075895.8.
Sep. 16, 2019 Office Action issued in Chinese Patent Application No. 201680009794.5.
Mar. 1, 2016 International Search Report issued in Patent Application No. PCT/JP2015/083589.
Dec. 13, 2016 Office Action issued in Japanese Patent Application No. 2016-545944.
Jul. 5, 2016 Office Action issued in Japanese Patent Application No. 2016-524543.
Jul. 5, 2016 Office Action issued in Japanese Patent Application No. 2016-524553.
Sep. 6, 2016 Office Action issued in Japanese Patent Application No. 2016-545944.
Sep. 27, 2016 Office Action issued in Japanese Patent Application No. 2016-524543.
Mar. 1, 2016 Written Opinion issued in International Patent Application No. PCT/JP2015/083589.
Jan. 31, 2018 Requirement for Restriction Election issued in U.S. Appl. No. 15/673,682.
Apr. 26, 2016 International Search Report issued in International Patent Application No. PCT/JP2016/053246.
May 10, 2016 International Search Report issued in International Patent Application No. PCT/JP2016/053247.
Feb. 9, 2016 International Search Report issued in International Patent Application No. PCT/JP2015/083592.
Feb. 9, 2016 International Search Report issued in International Patent Application No. PCT/JP2015/083591.
U.S. Appl. No. 15/674,153, filed Aug. 10, 2017 in the name of Hideto Yoshimine.
U.S. Appl. No. 15/673,682, filed Aug. 10, 2017 in the name of Masahiro Sakai.
U.S. Appl. No. 15/876,730, filed Jan. 22, 2018 in the name of Masahiro Sakai.
Aug. 17, 2018 extended Search Report issued in European Patent Application No. 16827452.0.
Sep. 16, 2019 Office Action Issued in U.S. Appl. No. 15/876,730.
Mar. 11, 2019 extended European Search Report issued in European Patent Application No. 16827453.8.
Mar. 14, 2019 extended European Search Report issued in European Patent Application No. 15898972.3.
Apr. 19, 2018 Office Action issued in U.S. Appl. No. 15/673,682.
May 23, 2018 Office Action issued in U.S. Appl. No. 15/674,153.
Jan. 23, 2018 Translation of International Preliminary Report on Patentability issued in International Application No. PCT/JP2015/083589.
Jan. 23, 2018 Translation of International Preliminary Report on Patentability issued in International Application No. PCT/JP2015/083591.
Jan. 23, 2018 Translation of International Preliminary Report on Patentability issued in International Application No. PCT/JP2015/083592.
Jan. 23, 2018 Translation of International Preliminary Report on Patentability issued in International Application No. PCT/JP2016/053246.
Jan. 23, 2018 Translation of International Preliminary Report on Patentability issued in International Application No. PCT/JP2016/053247.
Oct. 16, 2018 Office Action issued in U.S. Appl. No. 15/674,153.

(56) References Cited

OTHER PUBLICATIONS

Nov. 7, 2018 Office Action Issued in U.S. Appl. No. 15/673,682.
Mar. 23, 2020 Office Action issued in Chinese Patent Application No. 201580075895.8.
Feb. 13, 2020 Office Action issued in U.S. Appl. No. 15/876,730.
Mar. 12, 2020 Office Action issued European Patent Application No. 15898971.5.
May 12, 2020 Office Action issued in Chinese Patent Application No. 201580081886.X.
Jun. 2, 2020 Office Action issued Chinese Patent Application No. 201680043367.9.
Sep. 24, 2020 Office Action issued European Patent Application No. 16827452.0.

* cited by examiner

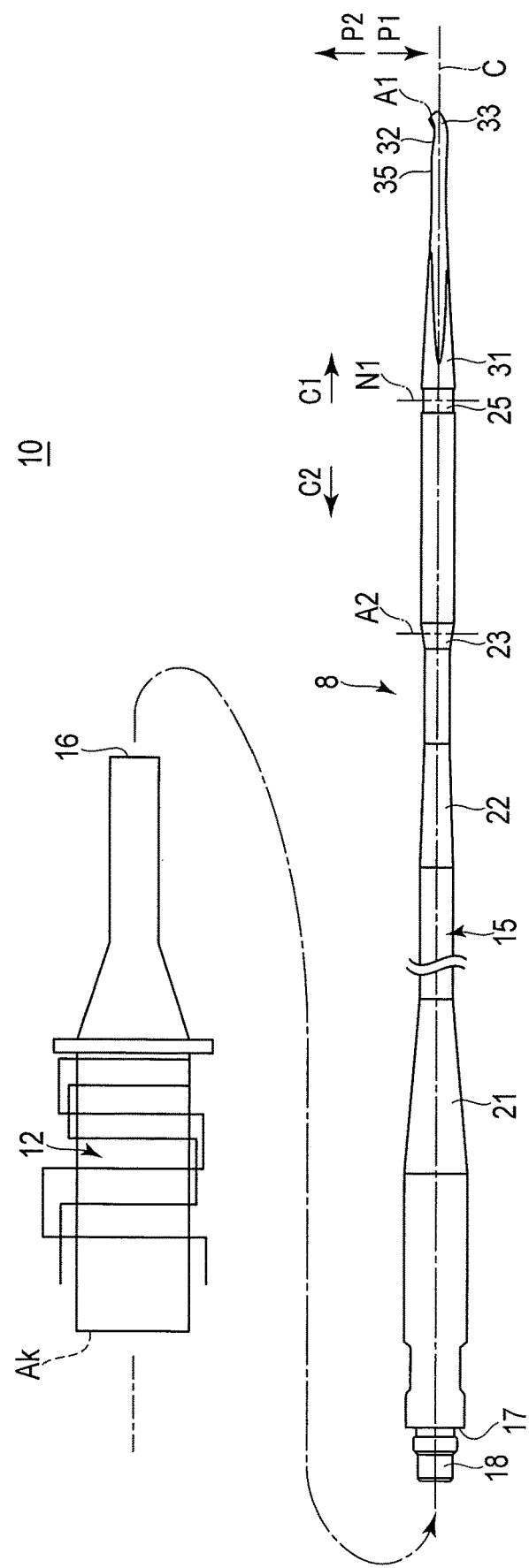
F I G. 2

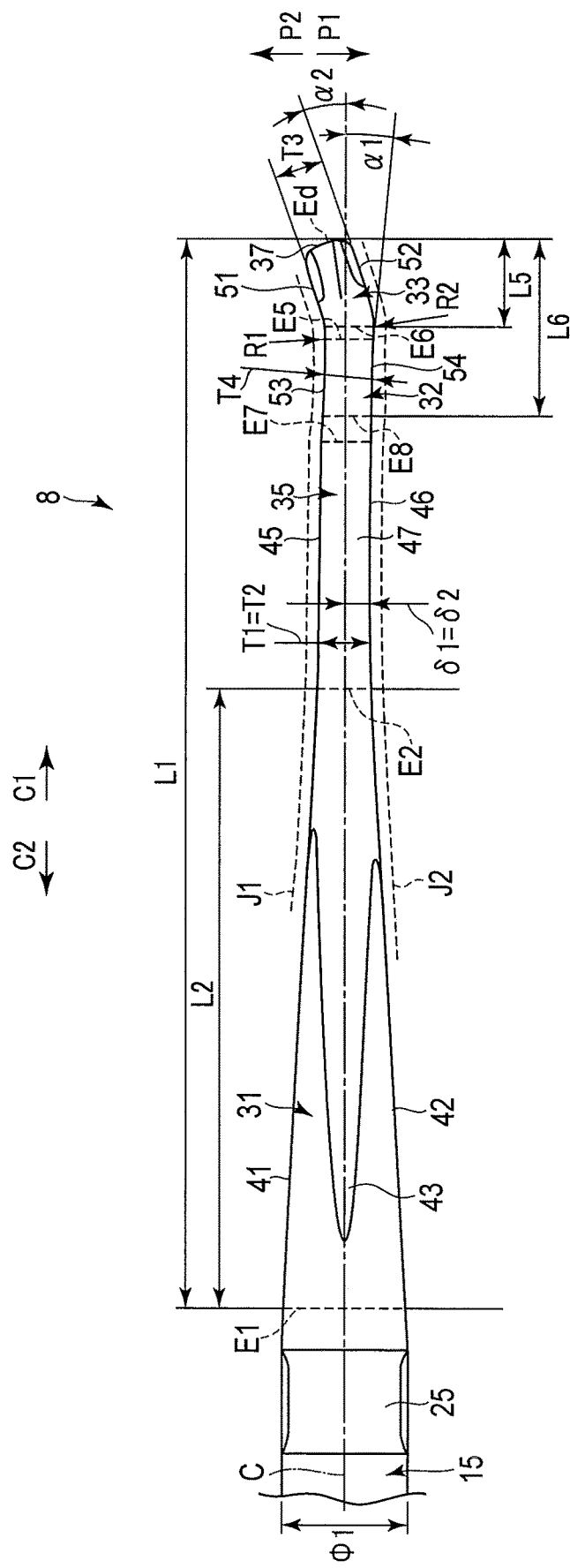
F I G. 13

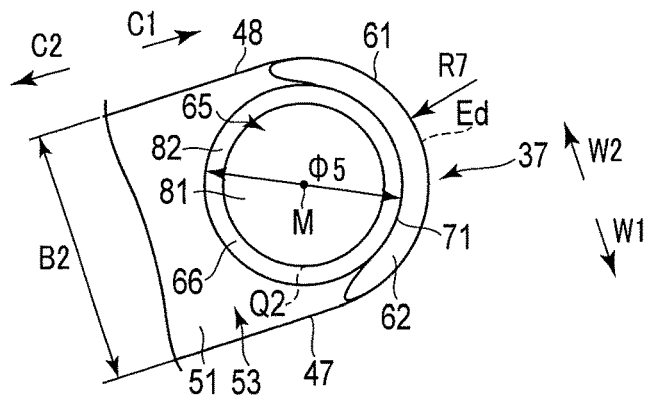
F I G. 15
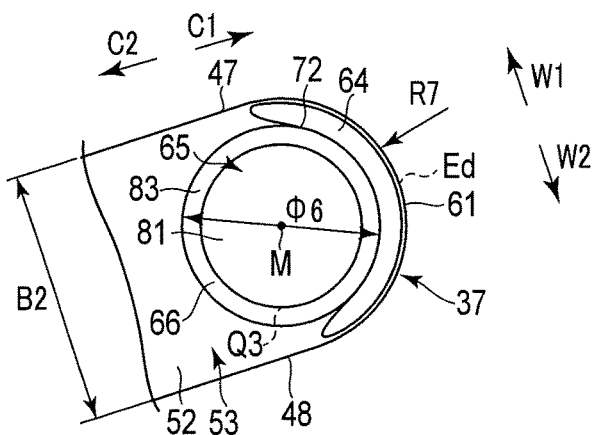
F I G. 16
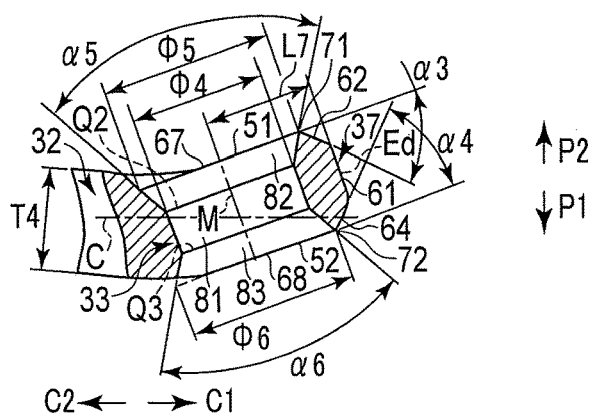
F I G. 17

ULTRASONIC PROBE

CROSS-REFERENCE TO RELATED APPLICATIONS

This is a Continuation Application of PCT Application No. PCT/JP2016/053247, filed Feb. 3, 2016 and based upon and claiming the benefit of priority from prior U.S. Provisional Application No. 62/196,158, filed Jul. 23, 2015, the entire contents of which are incorporated herein by reference.

BACKGROUND OF THE INVENTION

1. Field of the Invention

The present invention relates to an ultrasonic probe which is used for surgery in a joint and which transmits ultrasonic vibration.

2. Description of the Related Art

Jpn. Pat. Appln. KOKAI Publication No. 2003-116870 discloses an ultrasonic treatment instrument including an ultrasonic probe (ultrasonic horn). In this ultrasonic treatment instrument, ultrasonic vibration generated in a vibration generating section (ultrasonic vibration mechanism) is transmitted from a proximal side to a distal side in the ultrasonic probe. In a distal portion of the ultrasonic probe, a scalpel portion is formed as an abrading blade. In a state where the abrading blade is in contact with a treated target, the ultrasonic vibration is transmitted to the scalpel portion, and the treated target (e.g. a bone or the like) is thereby abraded.

BRIEF SUMMARY OF THE INVENTION

According to one aspect of the invention, an ultrasonic probe which is used for surgery in a joint and which transmits ultrasonic vibration from a proximal side to a distal side, the ultrasonic probe including: a probe main body which extends along a linear longitudinal axis from the proximal side toward the distal side and to which an ultrasonic transducer generating the ultrasonic vibration is connected on the proximal side; a narrowed portion which is continuous with the distal side of the probe main body and whose sectional area perpendicular to the longitudinal axis decreases from the proximal side toward the distal side; a first bent extending portion which is provided on the distal side with respect to the narrowed portion and which extends in such a state as to bend toward a first crossing direction side with respect to the longitudinal axis when the first crossing direction crossing the longitudinal axis is defined; a second bent extending portion which is continuous with the distal side of the first bent extending portion and which extends in such a state as to bend toward a second crossing direction side with respect to the longitudinal axis when the second crossing direction opposite to the first crossing direction is defined; and a blade portion which is provided in the second bent extending portion and with which a bone or a cartilage is abraded in the joint by use of the ultrasonic vibration, wherein in a projection seen from the distal side, the narrowed portion, the first bent extending portion, and the second bent extending portion are located within a minimum inside diameter of a sheath through which the ultrasonic probe is inserted.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic diagram showing a configuration of a vibrating body unit according to the first embodiment;

FIG. 13 is a schematic diagram in which the distal portion of the ultrasonic probe according to a second embodiment is seen from one side of the width direction;

FIG. 15 is a schematic diagram in which the second bent extending portion according to the second embodiment is seen from the side of the first bent outer surface in the thickness direction;

FIG. 16 is a schematic diagram in which the second bent extending portion according to the second embodiment is seen from the side of a second bent outer surface in the thickness direction;

FIG. 17 is a sectional view schematically showing the second bent extending portion according to the second embodiment in the section perpendicular to the width direction at the substantially middle position of the second bent extending portion in the width direction;

DETAILED DESCRIPTION OF THE INVENTION

First Embodiment

Figure 1:
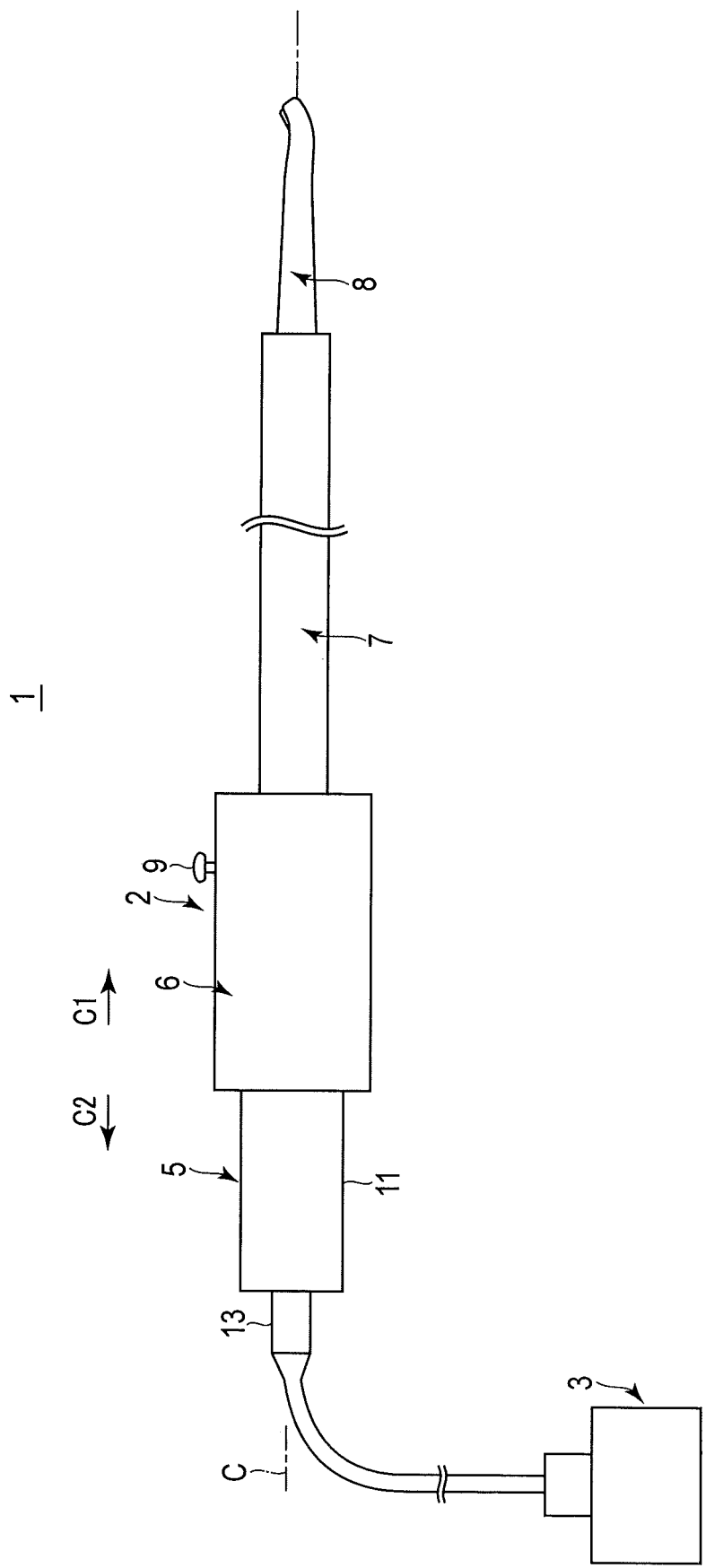
FIG. 1 is a schematic diagram showing an ultrasonic treatment system according to a first embodiment.

A first embodiment of the present invention is described with reference to FIG. 1 to FIG. 12. FIG. 1 is a diagram showing an ultrasonic treatment system 1 according to the present embodiment. FIG. 2 is a diagram showing a configuration of a vibrating body unit 10 formed by an ultrasonic probe 8 and an ultrasonic transducer 12 which will be described later. As shown in FIG. 1, the ultrasonic treatment system 1 includes an ultrasonic treatment instrument (handpiece) 2, an energy controller 3, and a transducer unit 5. The ultrasonic treatment instrument 2 has a substantially linear longitudinal axis C. Herein, one side of a direction (longitudinal direction) along the longitudinal axis C is a distal side (an arrow C1 side), and a side opposite to the distal side is a proximal side (an arrow C2 side). Further, the ultrasonic treatment instrument 2 is used for surgery to abrade a bone or a cartilage in a joint such as a knee joint, a shoulder joint, and an elbow joint.

The ultrasonic treatment instrument 2 includes a holdable housing 6, a sheath 7, and the ultrasonic probe 8 for joints. The housing 6 extends along the longitudinal axis C, and the sheath 7 is coupled to the housing 6 from the distal side. The sheath 7 extends along the longitudinal axis C, and is a hollow member having the longitudinal axis C as a substantially central axis. The ultrasonic probe (vibration transmitting member) 8 is inserted through the sheath 7. A distal portion of the ultrasonic probe 8 protrudes from a distal end of the sheath 7 toward the distal side. Further, an operation button 9 which is an energy operation input portion to be operated by a surgeon is attached to the housing 6.

The transducer unit 5 includes a transducer case 11, and the ultrasonic transducer 12 (see FIG. 12) provided inside the transducer case 11. The transducer case 11 is coupled to the housing 6 from the proximal side. Further, inside the housing 6, the ultrasonic transducer 12 is connected to the ultrasonic probe 8 from the proximal side. The transducer unit 5 is connected to the energy controller 3 via a cable 13. The energy controller 3 includes an electric power source, a conversion circuit which converts electric power from the electric power source into electric energy to be supplied to the ultrasonic transducer 12, a processor or the like (controller) including a central processing unit (CPU), an application specific integrated circuit (ASIC), or the like, and a storage medium such as a memory. The energy controller 3 outputs the electric energy to the ultrasonic transducer 12 by detecting an input of an operation in the operation button 9.

Ultrasonic vibration is generated in the ultrasonic transducer 12 by the supply of the electric energy to the ultrasonic transducer 12. Further, the generated ultrasonic vibration is transmitted to the ultrasonic probe 8, and the ultrasonic vibration is transmitted from the proximal side toward the distal side in the ultrasonic probe 8. At this moment, the vibrating body unit 10 formed by the ultrasonic transducer 12 and the ultrasonic probe 8 vibrates (longitudinally vibrates) at any frequency within a specified frequency range. For example, the vibrating body unit 10 is designed to longitudinally vibrate at 47 kHz by the transmission of the ultrasonic vibration, and, actually, longitudinally vibrates at any frequency within a frequency range of 46 kHz or more to 48 kHz or less. Further, as shown in FIG. 2, in a state where the vibrating body unit 10 longitudinally vibrates at any frequency within the specified frequency range, a vibration antinode Al of the longitudinal vibration is located at a distal end of the ultrasonic probe 8, and a vibration antinode Ak of the longitudinal vibration is located at a proximal end of the ultrasonic transducer 12. Herein, the vibration antinode Al is located most distally among vibration antinodes Ai (i=1, 2, . . . , and k) of the longitudinal vibration, and the vibration antinode Ak is located most proximally among the vibration antinodes Ai.

The ultrasonic transducer 12 extends to have the substantially linear longitudinal axis C as a substantially central axis. A transducer abutment surface 16 is formed at a distal end of the ultrasonic transducer 12. The ultrasonic probe 8 includes a probe main body 15 extending along the substantially linear longitudinal axis C. The probe main body 15 extends to have the longitudinal axis C as a substantially central axis. A probe abutment surface 17 is formed at a proximal end of the probe main body 15. Further, an engagement protrusion 18 protruding from the probe abutment surface 17 (a proximal end of the probe main body 15) toward the proximal side is provided in the ultrasonic probe 8. The engagement protrusion 18 engages with an engagement groove (not shown) provided in the ultrasonic transducer 12 (e.g. an external screw of the engagement protrusion 18 screws into an internal screw of the engagement groove), whereby the ultrasonic probe 8 is connected to the distal side of the ultrasonic transducer 12. In a state where the ultrasonic probe 8 is connected to the ultrasonic transducer 12, the probe abutment surface 17 of the probe main body 15 abuts on the transducer abutment surface 16 of the ultrasonic transducer 12, and the ultrasonic vibration is transmitted to the ultrasonic probe 8 (the probe main body 15) from the ultrasonic transducer 12 through the transducer abutment surface 16 and the probe abutment surface 17.

The probe main body 15 includes a horn 21, a horn 22 provided on the distal side with respect to the horn 21, a sectional area increasing portion 23 provided on the distal side with respect to the horn 22, and a supported portion 25 provided on the distal side with respect to the sectional area increasing portion 23. In each of the horns 21 and 22, a sectional area perpendicular to the longitudinal axis C decreases from the proximal side toward the distal side. In a state where the vibrating body unit 10 longitudinally vibrates at any frequency within the specified frequency range (e.g. a range of 46 kHz or more to 48 kHz or less), all of the vibration antinodes Ai of the longitudinal vibration are located apart from the horns 21 and 22. Thus, the amplitude of the longitudinal vibration is increased in the horns 21 and 22. In the sectional area increasing portion 23, a sectional area perpendicular to the longitudinal axis C increases from the proximal side toward the distal side. In a state where the vibrating body unit 10 longitudinally vibrates at any frequency within the specified frequency range, a vibration antinode A2 of the longitudinal vibration is located in the sectional area increasing portion 23. Thus, the amplitude of the longitudinal vibration hardly decreases in the sectional area increasing portion 23. In a state where the vibrating body unit 10 longitudinally vibrates at any frequency within the specified frequency range, the amplitude of the longitudinal vibration is 80 to 90 µm at the vibration antinode Al located at the distal end of the ultrasonic probe 8, for example, when the longitudinal vibration having an amplitude of 10 to 18 µm is transmitted to the proximal end of the probe main body 15 (the probe abutment surface 17). Note that the vibration antinode A2 is located second distally among the vibration antinodes Ai of the longitudinal vibration.

Furthermore, the supported portion 25 is formed into a groove shape depressed toward an inner peripheral side all around the longitudinal axis C, and an elastic member (not shown) is attached to an outer peripheral surface of the supported portion 25. In the supported portion 25, the ultrasonic probe 8 is supported, via its elastic member, by the sheath 7. In a state where the vibrating body unit 10 longitudinally vibrates at any frequency within the specified frequency range (a range of 46 kHz or more to 48 kHz or less), a vibration node Nl of the longitudinal vibration is located in the supported portion 25. Herein, the vibration node Nl is located most distally among vibration nodes Nj (j=1, 2, . . . , and k−1) of the longitudinal vibration. Further, the distal end of the sheath 7 is located on the distal side with respect to the supported portion 25. Thus, in a state where the vibrating body unit 10 longitudinally vibrates at any frequency within the specified frequency range, the most distal vibration node Nl is located within the sheath 7.

Figure 3:
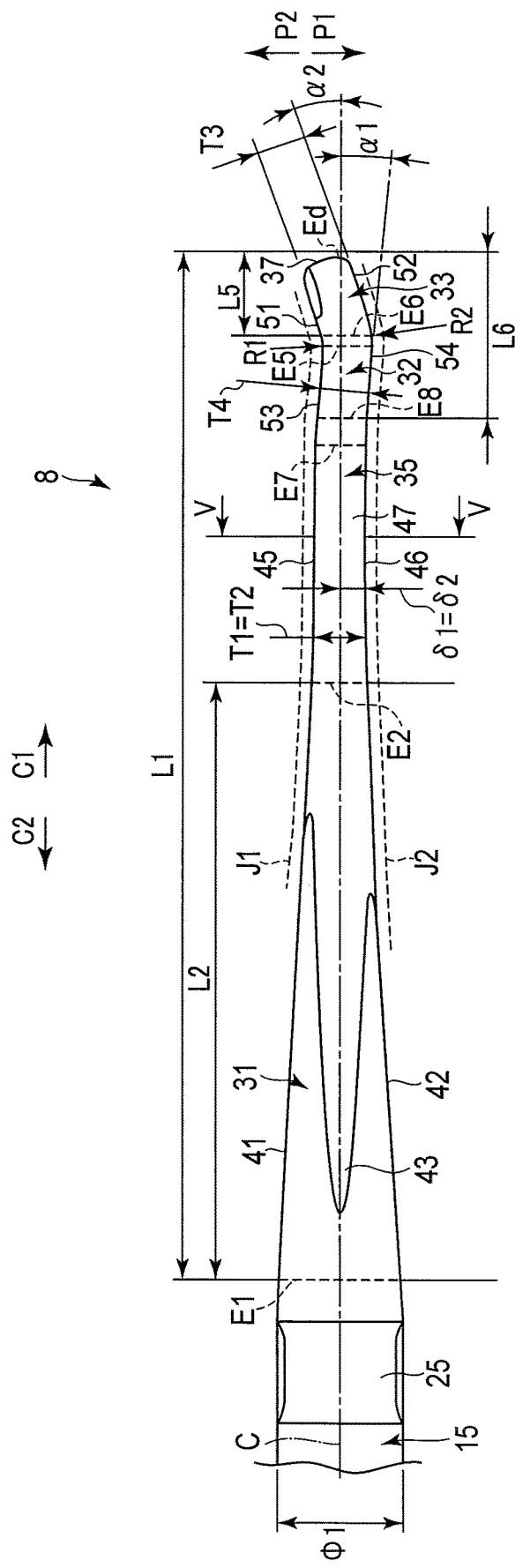
FIG. 3 is a schematic diagram in which a distal portion of an ultrasonic probe according to the first embodiment is seen from one side of a width direction.
Figure 4:
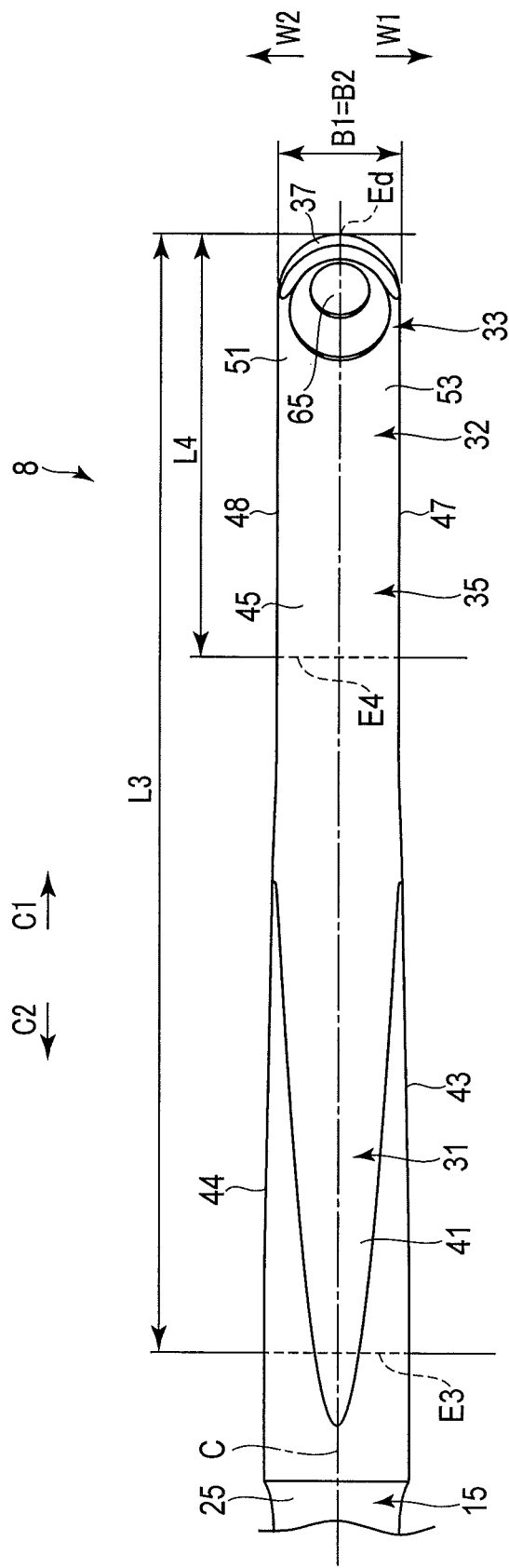
FIG. 4 is a schematic diagram in which the distal portion of the ultrasonic probe according to the first embodiment is seen from a second crossing direction side.

FIGS. 3 and 4 are diagrams showing a configuration of the distal portion of the ultrasonic probe 8. Herein, there are defined a first crossing direction (a direction of an arrow P1) which is one direction crossing (substantially perpendicular to) the longitudinal axis C, and a second crossing direction (a direction of an arrow P2) opposite to the first crossing direction (first perpendicular direction). There is also defined a width direction (a direction of an arrow W1 and an arrow W2) of the ultrasonic probe 8 crossing (substantially perpendicular to) the longitudinal axis C and substantially perpendicular to (crossing) the first crossing direction (first perpendicular direction) and the second crossing direction (second perpendicular direction). Each of FIGS. 2 and 3 is a diagram in which the ultrasonic probe 8 is seen from one side (e.g. an arrow W1 side shown in FIG. 4) of the width direction, and FIG. 4 is a diagram in which the ultrasonic probe 8 is seen from the second crossing direction side.

As shown in FIG. 2 to FIG. 4, the ultrasonic probe 8 includes a narrowed portion 31 continuous with the distal side of the probe main body 15, a first bent extending portion 32 provided on the distal side with respect to the narrowed portion 31, and a second bent extending portion 33 continuous with the distal side of the first bent extending portion 32. In the present embodiment, a treatment portion with which a treated target is treated is formed by the bent extending portions 32 and 33. Further, in the ultrasonic probe 8, an intermediate extending portion 35 is continuous between the narrowed portion 31 and the first bent extending portion 32 in a direction along the longitudinal axis C. A boundary position E1 between the probe main body 15 and the narrowed portion 31 (i.e. a distal end of the probe main body 15 and a proximal end of the narrowed portion 31) is located on the distal side with respect to the supported portion 25 of the probe main body 15.

Furthermore, the distal end of the sheath 7 is located on the distal side with respect to the boundary position E1 between the probe main body 15 and the narrowed portion 31. Moreover, an outer peripheral side of a proximal portion of the narrowed portion 31 is covered with the sheath 7. However, outer peripheries of parts of the narrowed portion 31 other than the proximal portion, the intermediate extending portion 35, the first bent extending portion 32, and the second bent extending portion 33 are not covered with the sheath 7. Therefore, in the ultrasonic probe 8, the parts of the narrowed portion 31 other than the proximal portion, the intermediate extending portion 35, the first bent extending portion 32, and the second bent extending portion 33 protrude from the distal end of the sheath 7 toward the distal side. Moreover, the second bent extending portion 33 includes a distal outer surface 37 forming a distal end Ed of the ultrasonic probe 8. In a certain example, a dimension L1 in the direction (longitudinal direction) along the longitudinal axis C from the distal end Ed of the ultrasonic probe 8 to the boundary position E1 between the probe main body 15 and the narrowed portion 31 is 29 to 31 mm.

The narrowed portion 31 includes a first narrowed outer surface 41 facing toward the second crossing direction side (arrow P2 side), a second narrowed outer surface 42 facing toward the first crossing direction side (arrow P1 side), a third narrowed outer surface 43 facing toward one side (the arrow W1 side) of the width direction, and a fourth narrowed outer surface 44 facing toward the other side (the arrow W2 side) of the width direction. Each of the narrowed outer surfaces 41 to 44 comes closer to the longitudinal axis C from the proximal side toward the distal side. Each of the narrowed outer surfaces 41 and 42 extends toward the distal side from the boundary position (first narrowing start position) E1 between the probe main body 15 and the narrowed portion 31 up to a narrowing end position (first narrowing end position) E2 in the direction along the longitudinal axis C. Therefore, between the boundary position E1 and the narrowing end position E2, the dimension of the narrowed portion 31 in the first crossing direction and the second crossing direction (i.e., a thickness direction of the narrowed portion 31) decreases from the proximal side toward the distal side. In a certain example, a dimension L2 in the direction along the longitudinal axis C from the boundary position E1 to the narrowing end position E2 is 14 to 18 mm.

Each of the narrowed outer surfaces 43 and 44 extends toward the distal side from a narrowing start position (second narrowing start position) E3 up to a narrowing end position (second narrowing end position) E4 in the direction along the longitudinal axis C. Therefore, between the narrowing start position E3 and the narrowing end position E4, the dimension of the narrowed portion 31 in the width direction of the narrowed portion 31 decreases from the proximal side toward the distal side. The narrowing start position E3 is located on the distal side with respect to the boundary position E1, and located on the proximal side with respect to the narrowing end position E2. Further, the narrowing end position E4 is located on the distal side with respect to the narrowing end position E2. In a certain example, a dimension L3 in the direction along the longitudinal axis C from the distal end Ed of the ultrasonic probe 8 to the narrowing start position E3 is 15 to 29.1 mm, and a dimension L4 in the direction along the longitudinal axis C from the distal end Ed of the ultrasonic probe 8 to the narrowing end position E4 is 10 to 11.1 mm.

Due to the configuration described above, the sectional area perpendicular to the longitudinal axis C decreases in the narrowed portion 31 from the proximal side toward the distal side. That is, between the boundary position E1 and the narrowing end position (second narrowing end position) E4, the sectional area of the narrowed portion 31 perpendicular to the longitudinal axis C decreases from the proximal side toward the distal side. In a certain example, at the boundary position E1 (i.e., the distal end of the probe main body 15), the sectional shape of the ultrasonic probe 8 perpendicular to the longitudinal axis C is in a circular shape having an outside diameter φ1 of 2.9 to 3.8 mm. In this example, at the narrowing end position (first narrowing end position) E2, a dimension T1 of the narrowed portion 31 in the first crossing direction and the second crossing direction (i.e. the thickness direction) is 1.5 to 1.6 mm. Further, in the present example, at the narrowing end position (second narrowing end position) E4, a dimension B1 of the narrowed portion 31 in the width direction is 2.7 to 3.2 mm. Moreover, in the present example, at the narrowing end position E2, a dimension δ1 in the first crossing direction from the longitudinal axis C up to the second narrowed outer surface 42 is 0.75 mm. When the outside diameter φ1, the dimensions T1 and B1, and the dimension δ1 are designed as described above, a center of gravity of the narrowed portion 31 slightly deviates toward the second crossing direction side from the longitudinal axis C. However, in the width direction of the narrowed portion 31, the center of gravity of the narrowed portion 31 does not deviate from the longitudinal axis C.

A first intermediate outer surface 45 facing toward the second crossing direction side is continuous with the distal side of the first narrowed outer surface 41, and a second intermediate outer surface 46 facing toward the first crossing direction side is continuous with the distal side of the second narrowed outer surface 42. Further, a third intermediate outer surface 47 facing toward one side of the width direction is continuous with the distal side of the third narrowed outer surface 43, and a fourth intermediate outer surface 48 facing toward the other side of the width direction is continuous with the distal side of the fourth narrowed outer surface 44. Therefore, the narrowing end position (first narrowing end position) E2 is a boundary position between the first narrowed outer surface 41 and the first intermediate outer surface 45, and is also a boundary position between the second narrowed outer surface 42 and the second intermediate outer surface 46. Further, the narrowing end position (second narrowing end position) E4 is a boundary position between the third narrowed outer surface 43 and the third intermediate outer surface 47, and is also a boundary position between the fourth narrowed outer surface 44 and the fourth intermediate outer surface 48. Herein, in an outer peripheral surface of the intermediate extending portion 35, a part facing toward the second crossing direction side is formed by the first intermediate outer surface 45, and a part facing toward the first crossing direction side is formed by the second intermediate outer surface 46. Moreover, in an outer peripheral surface of the intermediate extending portion 35, a part facing toward one side of the width direction is formed by the third intermediate outer surface 47, and a part facing toward the other side of the width direction is formed by the fourth intermediate outer surface 48.

Each of the intermediate outer surfaces 45 to 48 extends substantially parallel to the longitudinal axis C along the longitudinal axis C. Further, each of the intermediate outer surfaces 47 and 48 extends toward the distal side from the narrowing end position E4 up to the distal outer surface 37 of the ultrasonic probe 8 (the second bent extending portion 33), and a distal end of each of the intermediate outer surfaces 47 and 48 is continuous with the distal outer surface 37.

Because the intermediate outer surfaces 45 and 46 are substantially parallel to the longitudinal axis C, a dimension (a dimension of the intermediate extending portion 35 in the thickness direction) T2 between the intermediate outer surfaces 45 and 46 in the first crossing direction and the second crossing direction is substantially the same as the dimension T1 of the narrowed portion 31 in the thickness direction at the narrowing end position E2. Further, a dimension δ2 in the first crossing direction from the longitudinal axis C up to the second intermediate outer surface 46 is substantially the same as the dimension δ1 in the first crossing direction from the longitudinal axis C up to the second narrowed outer surface 42 at the narrowing end position E2. Moreover, because the intermediate outer surfaces 47 and 48 are substantially parallel to the longitudinal axis C, a dimension (a dimension of each of the intermediate extending portion 35 and the bent extending portions 32 and 33 in the width direction) B2 between the intermediate outer surfaces 47 and 48 in the width direction of the ultrasonic probe 8 is substantially the same as the dimension B1 of the narrowed portion 31 in the width direction at the narrowing end position E4. Further, the intermediate extending portion 35 whose outer peripheral surface is formed by the intermediate outer surfaces 45 to 48 extends substantially parallel to the longitudinal axis C, and in the intermediate extending portion 35, the sectional area perpendicular to the longitudinal axis C is substantially uniform over the entire length in the direction along the longitudinal axis C.

In a certain example, the dimension T2 is 1.5 to 1.6 mm, the dimension B2 is 2.7 to 3.2 mm, and the dimension δ2 is 0.75 mm. In this example, a center of gravity of the intermediate extending portion 35 slightly deviates toward the second crossing direction from the longitudinal axis C. However, in the width direction of the intermediate extending portion 35 (the ultrasonic probe 8), the center of gravity of the intermediate extending portion 35 does not deviate from the longitudinal axis C.

The first bent extending portion 32 extends in such a state as to bend toward the first crossing direction side with respect to the longitudinal axis C. The first bent extending portion 32 has a bending angle α1 to the longitudinal axis C toward the first crossing direction side. That is, a direction rotated from the distal side toward the first crossing direction side by the bending angle α1 is an extending direction of the first bent extending portion 32. In a certain example, the bending angle α1 is 5°.

The second bent extending portion 33 extends in such a state as to bend toward the second crossing direction side with respect to the longitudinal axis C. The second bent extending portion 33 has a bending angle α2 to the longitudinal axis C toward the second crossing direction side. That is, a direction rotated from the distal side toward the second crossing direction side by the bending angle α2 is an extending direction of the second bent extending portion 33. In a certain example, the bending angle α2 is 20°.

The second bent extending portion 33 includes a first bent outer surface 51 facing toward the second crossing direction side (arrow P2 side), and a second bent outer surface 52 facing toward the first crossing direction side (arrow P1 side). The bent outer surfaces 51 and 52 are substantially parallel to each other, and each of the bent outer surfaces 51 and 52 extends in such a state as to bend toward the second crossing direction side at the bending angle α2 to the longitudinal axis C. In a certain example, a dimension T3 of the second bent extending portion 33 in the thickness direction between the first bent outer surface 51 and the second bent outer surface 52 is 1.5 mm. The first bent outer surface 51 extends toward the distal side from a bending start position (first bending start position) E5 up to the distal outer surface 37 of the second bent extending portion 33 in the direction along the longitudinal axis C, and a distal end of the first bent outer surface 51 is continuous with the distal outer surface 37. Further, the second bent outer surface 52 extends toward the distal side from a bending start position (second bending start position) E6 up to the distal outer surface 37 of the second bent extending portion 33 in the direction along the longitudinal axis C, and a distal end of the second bent outer surface 52 is continuous with the distal outer surface 37.

The first bent extending portion 32 includes a third bent outer surface 53 facing toward the second crossing direction side (arrow P2 side), and a fourth bent outer surface 54 facing toward the first crossing direction side (arrow P1 side). The bent outer surfaces 53 and 54 are substantially parallel to each other, and each of the bent outer surfaces 53 and 54 extends in such a state as to bend toward the first crossing direction side at the bending angle α1 to the longitudinal axis C. In a certain example, a dimension T4 of the first bent extending portion 32 in the thickness direction between the third bent outer surface 53 and the fourth bent outer surface 54 is 1.5 mm.

At the bending start position (first bending start position) E5, the third bent outer surface 53 is continuous with the proximal side of the first bent outer surface 51. Therefore, the bending start position E5 is a boundary position between the first bent outer surface 51 and the third bent outer surface 53. Further, at the bending start position (second bending start position) E6, the fourth bent outer surface 54 is continuous with the proximal side of the second bent outer surface 52. Therefore, the bending start position E6 is a boundary position between the second bent outer surface 52 and the fourth bent outer surface 54. The bedding start position E6 of the second bent outer surface 52 is located on the distal side with respect to the bending start position E5 of the first bent outer surface 51. Moreover, in a certain example, a dimension L5 in the direction along the longitudinal axis C up to the distal end Ed of the second bent extending portion 33 (the ultrasonic probe 8) from the bending start position E6 which is the boundary position between the second bent outer surface 52 and the fourth bent outer surface 54 is 2.35 mm.

At the bending start position E5, a part between the first bent outer surface 51 and the third bent outer surface 53 is formed into a curved surface shape having a bending radius (bending r) R1. Further, at the bending start position E6, a part between the second bent outer surface 52 and the fourth bent outer surface 54 is formed into a curved surface shape having a bending radius (bending r) R2. In a certain example, the bending radius R1 is 2 mm, and the bending radius R2 is 3.5 mm.

The third bent outer surface 53 extends toward the distal side from a bending start position (third bending start position) E7. At the bending start position E7, the first intermediate outer surface 45 is continuous with the proximal side of the third bent outer surface 53. Therefore, the bending start position E7 is a boundary position between the third bent outer surface 53 and the first intermediate outer surface 45. Further, the fourth bent outer surface 54 extends toward the distal side from a bending start position (fourth bending start position) E8. At the bending start position E8, the second intermediate outer surface 46 is continuous with the proximal side of the fourth bent outer surface 54. Therefore, the bending start position E8 is a boundary position between the fourth bent outer surface 54 and the second intermediate outer surface 46. The bending start position E8 of the fourth bent outer surface 54 is located on the distal side with respect to the bending start position E7 of the third bent outer surface 53. Further, the bending start position E8 of the fourth bent outer surface 54 is located on the proximal side with respect to the bending start position E5 of the first bent outer surface 51, and the bending start position E7 of the third bent outer surface 53 is located on the distal side with respect to the narrowing end position E4 of the narrowed outer surfaces 43 and 44. In a certain example, a dimension L6 in the direction along the longitudinal axis C up to the distal end Ed of the second bent extending portion 33 (the ultrasonic probe 8) from the bending start position E8 which is the boundary position between the fourth bent outer surface 54 and the second intermediate outer surface 46 is 5 to 6.5 mm.

Figure 5:
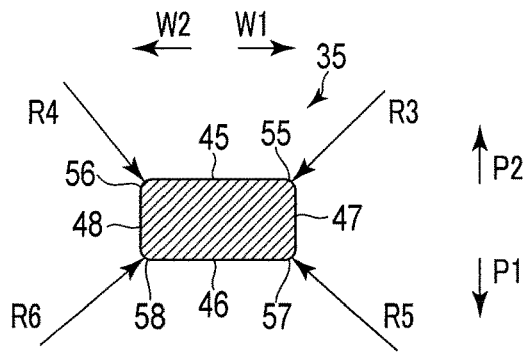
FIG. 5 is a sectional view taken along the line V-V in FIG. 3.

FIG. 5 is a sectional view taken along the line V-V in FIG. 3. FIG. 5 shows a section perpendicular to the longitudinal axis C between the narrowing end position (second narrowing end position) E4 and the bending start position (third bending start position) E7 in the direction along the longitudinal axis C (i.e. in the intermediate extending portion 35). As shown in FIG. 5, in the intermediate extending portion 35, a curved surface (first curved surface) 55 having a bending radius R3 is formed between the first intermediate outer surface 45 and the third intermediate outer surface 47, and a curved surface (second curved surface) 56 having a bending radius R4 is formed between the first intermediate outer surface 45 and the fourth intermediate outer surface 48. Moreover, in the intermediate extending portion 35, a curved surface (third curved surface) 57 having a bending radius R5 is formed between the second intermediate outer surface 46 and the third intermediate outer surface 47, and a curved surface (fourth curved surface) 58 having a bending radius R6 is formed between the second intermediate outer surface 46 and the fourth intermediate outer surface 48. In a certain example, each of the bending radii R3 and R4 is 0.3 mm, and each of the bending radii R5 and R6 is 0.3 to 0.5 mm.

Furthermore, each of the curved surfaces 55 to 58 is not formed in the intermediate extending portion 35 alone, and extends in a range between the second bent extending portion 33 and a distal portion of the narrowed portion 31 in the direction along the longitudinal axis C. For example, each of the curved surfaces 55 and 56 extends in a range indicated by a broken line J1 in FIG. 3, and each of the curved surfaces 57 and 58 extends in a range indicated by a broken line J2 in FIG. 3. Hence, in the distal portion of the narrowed portion 31 and in each of the intermediate extending portion 35 and the bent extending portions 32 and 33, the curved surface 55 is formed between a part of the outer surface facing toward the first crossing direction side and a part facing toward one side (the arrow W1 side) of the width direction, and the curved surface 56 is formed between the part of the outer surface facing toward the first crossing direction side and a part facing toward the other side (the arrow W2 side) of the width direction. Moreover, in the distal portion of the narrowed portion 31 and in each of the intermediate extending portion 35 and the bent extending portions 32 and 33, the curved surface 57 is formed between a part of the outer surface facing toward the second crossing direction side and a part facing toward one side (the arrow W1 side) of the width direction, and the curved surface 58 is formed between the part of the outer surface facing toward the second crossing direction side and a part facing toward the other side (the arrow W2 side) of the width direction.

Figure 6:
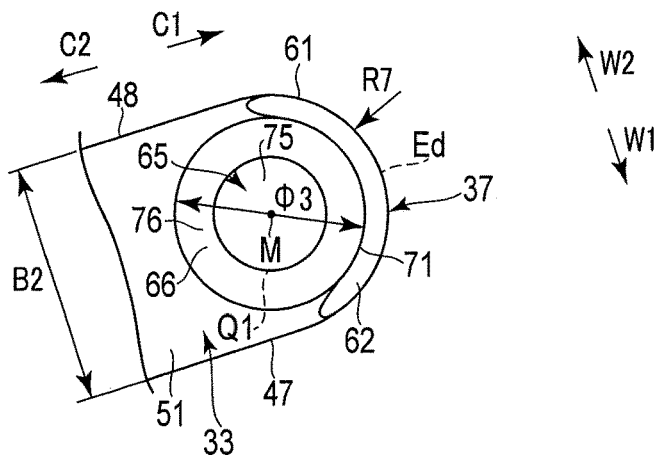
FIG. 6 is a schematic diagram in which a second bent extending portion according to the first embodiment is seen from the side of a first bent outer surface in a thickness direction.
Figure 7:
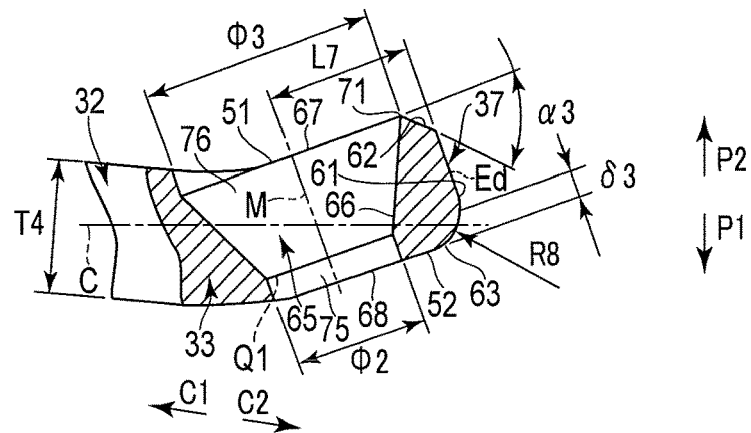
FIG. 7 is a sectional view schematically showing the second bent extending portion according to the first embodiment in a section perpendicular to the width direction at a substantially middle position of the second bent extending portion in the width direction.

FIG. 6 and FIG. 7 are diagrams showing a configuration of the second bent extending portion 33. FIG. 6 shows a state seen from the side of the first bent outer surface 51 (the second crossing direction side) in the thickness direction. FIG. 7 shows a section perpendicular to the width direction at a substantially middle position of the second bent extending portion 33 in the width direction. As shown in FIG. 6 and FIG. 7, the distal outer surface 37 of the second bent extending portion 33 includes a distal curved surface 61 formed into a curved surface shape having a radius R7 seen from the side of the first bent outer surface 51. The distal end Ed of the second bent extending portion 33 (the ultrasonic probe 8) is formed by the distal curved surface 61, and the distal end of each of the intermediate outer surfaces 47 and 48 is continuous with the distal curved surface 61. The distal curved surface 61 extends along the thickness direction of the second bent extending portion 33, and is substantially perpendicular to the bent outer surfaces 51 and 52 (the extending direction of the second bent extending portion 33). In a certain example, the radius R7 is 1.35 to 1.6 mm.

Furthermore, an inclined surface 62 is formed between the distal curved surface 61 and the first bent outer surface 51. The inclined surface 62 extends in such a state as to incline with respect to the thickness direction of the second bent extending portion 33 and incline with respect to the first bent outer surface 51 (the extending direction of the second bent extending portion 33). In a certain example, an inclination angle α3 of the inclined surface 62 with respect to the first bent outer surface 51 is 45°. Further, an intermediate curved surface 63 is formed between the distal curved surface 61 and the second bent outer surface 52. The intermediate curved surface 63 has a bending radius R8 in a section perpendicular to the width direction of the second bent extending portion 33. In a certain example, the bending radius R8 is 0.3 to 0.5 mm.

Moreover, a through-hole 65 pierced in the second bent extending portion 33 in the thickness direction from the first bent outer surface 51 up to the second bent outer surface 52 is formed in the second bent extending portion 33. The through-hole 65 extends along a hole central axis M, and has a hole defining surface 66 as an inner peripheral surface of the through-hole 65. An extending direction (a direction along the hole central axis M) of the through-hole 65 is substantially perpendicular to the extending direction of the second bent extending portion 33 (the bent outer surfaces 51 and 52), and is substantially parallel to the thickness direction of the second bent extending portion 33. Further, the through-hole 65 has an opening (first opening) 67 which is open in the first bent outer surface 51, and an opening (second opening) 68 which is open in the second bent outer surface 52. In a certain example, a dimension L7 from the hole central axis M of the through-hole 65 up to the distal end Ed of the second bent extending portion 33 (the ultrasonic probe 8) in the extending direction of the second bent extending portion 33 is 1.35 to 1.6 mm.

In the first bent outer surface 51, a part of the hole defining surface 66 is continuous with the inclined surface 62 at an opening edge of the opening 67 of the through-hole 65. Further, an abrading blade (first abrading blade) 71 is formed as a blade portion at a boundary between the hole defining surface 66 and the inclined surface 62. Therefore, in the first bent outer surface 51, the abrading blade 71 is formed in a part of the opening edge of the opening 67 of the through-hole 65. The abrading blade 71 is formed as described above, and is therefore formed into a substantially arc shape around the hole central axis M. Further, the abrading blade 71 is formed over a predetermined angular range around the hole central axis M in a part located on the distal side with respect to the hole central axis M.

The through-hole 65 has a circular-column-shaped portion 75 and a truncated-cone-shaped portion 76. The circular-column-shaped portion 75 extends toward the side of the first bent outer surface 51 from the second bent outer surface 52, and the truncated-cone-shaped portion 76 is continuous with the first bent outer surface 51 side of the circular-column-shaped portion 75. In the circular-column-shaped portion 75, the sectional area of the through-hole 65 perpendicular to the extending direction of the through-hole 65 is substantially uniform over the entire length in the extending direction (the direction along the hole central axis M) of the through-hole 65. In a certain example, a diameter φ2 of the through-hole 65 in the circular-column-shaped portion 75 is 1 to 1.5 mm. Further, a boundary position Q1 between the circular-column-shaped portion 75 and the truncated-cone-shaped portion 76 is defined in the through-hole 65. The second bent outer surface 52 is closer from the boundary position Q1 than the first bent outer surface 51. In a certain example, a dimension 63 in the extending direction of the through-hole 65 (the thickness direction of the second bent extending portion 33) from the second bent outer surface 52 up to the boundary position Q1 is 0.3 mm.

The truncated-cone-shaped portion 76 extends from the boundary position Q1 up to the abrading blade 71 formed on the opening edge of the opening 67 in the extending direction of the through-hole 65. In the truncated-cone-shaped portion 76, the sectional area of the through-hole 65 perpendicular to the extending direction of the through-hole 65 increases toward the abrading blade 71 (the first bent outer surface 51 side). For instance, in an example in which the diameter φ2 of the through-hole 65 in the circular-column-shaped portion 75 (i.e. the boundary position Q1) is 1.5 mm, a diameter φ3 of the through-hole 65 in the abrading blade 71 increases to 2.6 mm, and in an example in which the diameter φ2 of the through-hole 65 is 1 mm, the diameter φ3 of the through-hole 65 in the abrading blade 71 increases to 2.1 mm.

Figure 8:
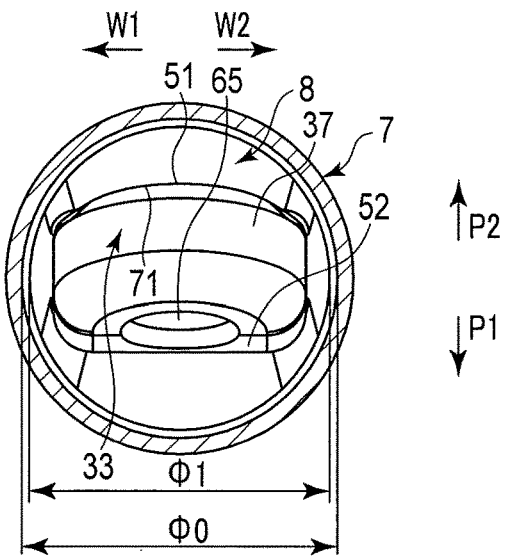
FIG. 8 is a schematic diagram in which a sheath and the ultrasonic probe according to the first embodiment are seen from a distal side.

FIG. 8 is a schematic diagram in which the sheath 7 and the ultrasonic probe 8 are seen from the distal side. As shown in FIG. 8, the sheath 7 has a minimum inside diameter φ0. The minimum inside diameter φ0 is larger than the outside diameter φ1 of the ultrasonic probe 8 at the boundary position E1 between the probe main body 15 and the narrowed portion 31. In an example in which the outside diameter φ1 is 3.8 mm, the minimum inside diameter φ0 of the sheath 7 is 4 mm. Further, in an example in which the outside diameter φ1 is 2.9 mm, the minimum inside diameter φ0 of the sheath 7 is 3.4 mm. In a projection seen from the distal side, the narrowed portion 31, the first bent extending portion 32, the second bent extending portion 33, and the intermediate extending portion 35 are located within the minimum inside diameter φ0 of the sheath 7. Moreover, in the present embodiment, in the projection seen from the distal side, the narrowed portion 31, the first bent extending portion 32, the second bent extending portion 33, and the intermediate extending portion 35 are located within the outside diameter φ1 of the ultrasonic probe 8 at the boundary position E1.

Next, functions and advantageous effects of the ultrasonic probe 8 and the ultrasonic treatment instrument 2 according to the present embodiment are described. The ultrasonic treatment system 1 is used for a treatment to abrade a bone or a cartilage in a joint such as a knee joint, a shoulder joint, and an elbow joint. In the treatment, a distal portion of the sheath 7 and the distal portion of the ultrasonic probe 8 are inserted into an articular cavity through a port (not shown) formed by a cannula or the like. Further, in the articular cavity, the abrading blade 71 of the second bent extending portion 33 is brought into contact with a treated target (e.g. an affected part formed in a bone or a cartilage). Further, in a state where the abrading blade 71 is in contact with the treated target, the surgeon performs an operational input with the operation button 9. Accordingly, ultrasonic vibration is generated in the ultrasonic transducer 12, and generated ultrasonic vibration is transmitted from the proximal side toward the distal side in the vibrating body unit 10. In a state where the ultrasonic vibration is being transmitted, the vibrating body unit 10 performs longitudinal vibration whose vibration direction is substantially parallel to the longitudinal axis C. The second bent extending portion 33 longitudinally vibrates in a state where the abrading blade 71 is in contact with the treated target, whereby the treated target (the bone, the cartilage, or the like) is abraded.

Figure 9:
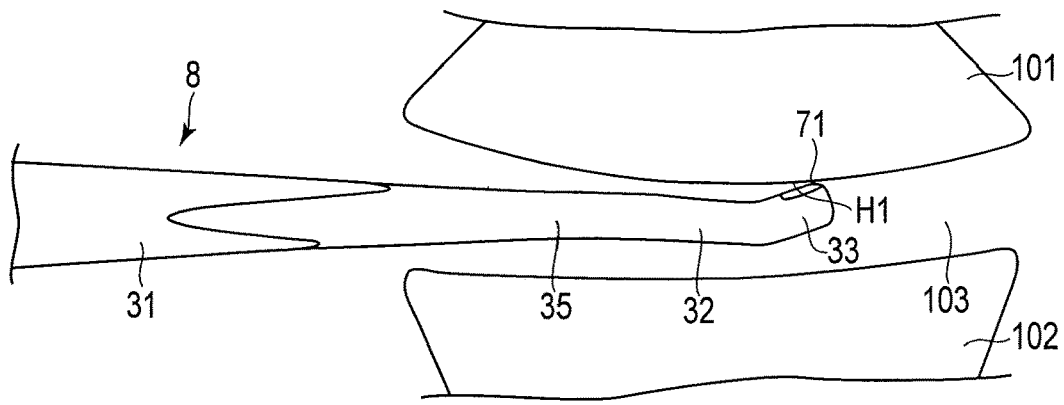
FIG. 9 is a schematic diagram showing one example of a state where a treated target is being abraded with an abrading blade according to the first embodiment.

FIG. 9 is a schematic diagram showing one example of a state where the treated target is abraded with the abrading blade 71. As shown in FIG. 9, in the articular cavity, the treated target may be abraded in a small space. For example, there is a case where an affected part H1 which is a treated target may be abraded in a small space 103 between a bone 101 and a bone 102. Because the abrading blade 71 needs to be brought into contact with the treated target (H1) in the small space 103, an angular range of an entry angle of the abrading blade 71 for the abrading blade 71 to approach the treated target (H1) (i.e. an approach angle of the abrading blade 71 to the treated target) is limited to a small range.

In the present embodiment, as described above, the first bent extending portion 32 is provided on the distal side with respect to the narrowed portion 31, and the first bent extending portion 32 extends in such a state as to bend toward the first crossing direction side with respect to the longitudinal axis C. Further, the second bent extending portion 33 is continuous with the distal side of the first bent extending portion 32, and the second bent extending portion 33 extends in such a state as to bend toward the second crossing direction side opposite to the first crossing direction side with respect to the longitudinal axis C. Further, the abrading blade 71 is formed in the first bent outer surface 51 facing toward the second crossing direction side in the second bent extending portion 33. Moreover, in the projection seen from the distal side, the narrowed portion 31, the first bent extending portion 32, the second bent extending portion 33, and the intermediate extending portion 35 are located within the minimum inside diameter ϕ0 of the sheath 7. The configuration described above prevents parts of the ultrasonic probe 8 other than the abrading blade 71 from interfering with tissues or the like other than the treated target (H1) (e.g. parts of the bone 101 other than the affected part H1) even in the small space (103) of the articular cavity in which the angular range of the approach angle to the treated target (H1) is limited to the small range. Thus, even in the small space (103), the abrading blade 71 which is the blade portion properly contacts the treated target (H1), and treatment performance in the treatment to abrade the treated target (H1) is ensured.

Furthermore, in the present embodiment, as shown in FIG. 8, in the projection seen from the distal side, the narrowed portion 31, the first bent extending portion 32, the second bent extending portion 33, and the intermediate extending portion 35 are located within the outside diameter ϕ1 of the ultrasonic probe 8 at the boundary position E1. This more effectively prevents parts of the ultrasonic probe 8 other than the abrading blade 71 from interfering with tissues or the like other than the treated target (H1) in the small space (103) of the articular cavity. Consequently, in the small space (103), the abrading blade 71 which is the blade portion more properly contacts the treated target (H1).

Moreover, in the present embodiment, the narrowed portion 31, the first bent extending portion 32, the second bent extending portion 33, and the intermediate extending portion 35 are configured to be located within the minimum inside diameter ϕ0 of the sheath 7, so that the ultrasonic probe 8 is easily inserted through the sheath 7. This reduces labor in the assembly of the ultrasonic treatment instrument 2.

Figure 10:
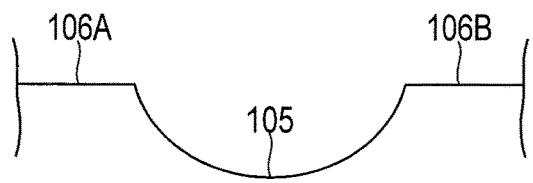
FIG. 10 is a schematic diagram showing the treated target abraded with the abrading blade according to the first embodiment.

FIG. 10 is a diagram showing the treated target abraded with the abrading blade 71. As described above, the abrading blade 71 is formed into the substantially arc shape around the hole central axis M. Therefore, in the present embodiment, as shown in FIG. 10, no edge having an acute angle is formed between a removed surface 105 in which the treated target is removed in the bone, the cartilage, or the like, and unremoved surfaces 106A and 106B adjacent to the removed surface 105. Further, because the abrading blade 71 is formed into the substantially arc shape, the removed surface 105 in which the treated target is removed becomes a depression whose section is substantially arc-shaped.

Furthermore, in the present embodiment, the first bent extending portion 32 extends in such a state as to bend toward the first crossing direction side with respect to the longitudinal axis C, whereas the second bent extending portion 33 extends in such a state as to bend toward the second crossing direction side with respect to the longitudinal axis C. Therefore, the whole center of gravity of the first bent extending portion 32 and the second bent extending portion 33 does not deviate greatly from the longitudinal axis C in the first crossing direction and the second crossing direction. Hence, in the present embodiment, even if the bent extending portions 32 and 33 are provided, lateral vibration (abnormal vibration) whose vibration direction is substantially parallel to the first crossing direction and the second crossing direction is reduced.

Figure 11:
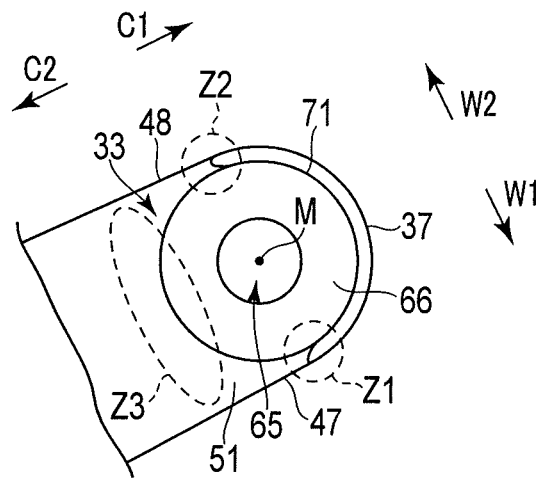
FIG. 11 is a schematic diagram showing a place of the second bent extending portion in which stress concentrates is seen from the side of the first bent outer surface in a state where the treated target is abraded with an abrading blade 71 according to the first embodiment.
Figure 12:
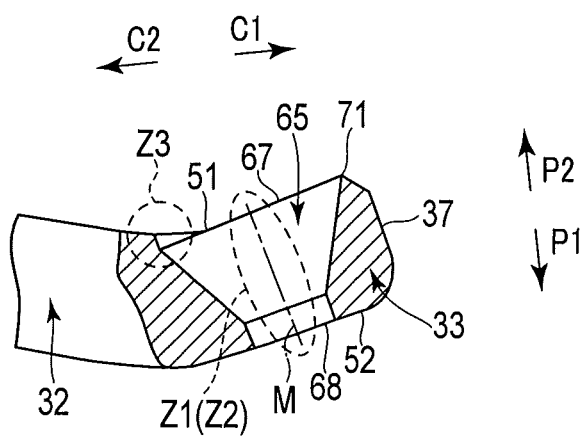
FIG. 12 is a sectional view schematically showing the place of the second bent extending portion in which stress concentrates, in the section perpendicular to the width direction passing through a hole central axis, in a state where the treated target is abraded with the abrading blade 71 according to the first embodiment.

FIG. 11 and FIG. 12 are diagrams showing places (zones Z1 to Z3) of the second bent extending portion 33 in which stress concentrates in a state where the treated target is abraded with the abrading blade 71. FIG. 11 shows a state seen from the first bent outer surface 51 side, and FIG. 12 shows in a section perpendicular to the width direction passing through the hole central axis M. In the present embodiment, the through-hole 65 is formed in the second bent extending portion 33, so that the sectional area perpendicular to the extending direction of the second bent extending portion 33 is smaller at substantially the same position as the hole central axis M and in its vicinity in the extending direction of the second bent extending portion 33. That is, at substantially the same position as the hole central axis M and in its vicinity in the extending direction of the second bent extending portion 33, a dimension (thickness) in the width directions of the hole defining surface 66 between the through-hole 65 and the third intermediate outer surface 47, and a dimension (thickness) in the width directions between the hole defining surface 66 of the through-hole 65 and the fourth intermediate outer surface 48 are smaller. Therefore, at substantially the same position as the hole central axis M and in its vicinity in the extending direction of the second bent extending portion 33, stress resulting from ultrasonic vibration (longitudinal vibration) concentrates in the zone Z1 between the hole defining surface 66 of the through-hole 65 and the third intermediate outer surface 47, and in the zone Z2 between the hole defining surface 66 of the through-hole 65 and the fourth intermediate outer surface 48.

Furthermore, in a state where the treated target is abraded with the abrading blade 71, the second bent extending portion 33 receives reaction force (tensile force) from the treated target toward the second bent outer surface 52 side (the first crossing direction side). At this moment, in the hole defining surface 66 of the through-hole 65 and its vicinity, stress caused by the reaction force from the treated target concentrates in the zones which are at smaller distances from the bending start position (first bending start position) E5 of the first bent outer surface 51. Therefore, the stress caused by the reaction force from the treated target concentrates in the zone Z3 which is located on a proximal portion of the opening edge of the opening 67 of the through-hole 65 and its vicinity.

In the present embodiment, a section perpendicular to the extending direction (the direction along the hole central axis M) of the through-hole 65 is substantially in a perfect circular shape. Thus, in a state where the treated target is abraded with the abrading blade 71, the zones Z1 and Z2 in which the stress resulting from ultrasonic vibration concentrates do not overlap the zone Z3 in which the stress caused by the reaction force from the treated target concentrates. Consequently, in the second bent extending portion 33, local generation of excessively high stress is prevented, and breakage of the ultrasonic probe 8 is effectively prevented.

Furthermore, in the through-hole 65, the truncated-cone-shaped portion 76 is formed from the boundary position Q1 to the abrading blade 71. Therefore, the angle of the abrading blade 71 is formed into an acute angle (sharply), and a dimension (thickness) from the distal outer surface 37 to the hole defining surface 66 of the through-hole 65 is larger in the extending direction of the second bent extending portion 33 in a zone apart from the abrading blade 71 in the thickness direction of the second bent extending portion 33, such as a zone between the boundary position Q1 and the second bent outer surface 52. That is, even if the abrading blade 71 is sharply formed, strength of the abrading blade 71 is ensured.

Second Embodiment

Next, a second embodiment of the present invention is described with reference to FIG. 13 to FIG. 19. The second embodiment concerns the following modification of the configuration according to the first embodiment. Note that the same reference numbers are given to the same parts as those in the first embodiment, and the description thereof is omitted.

Figure 14:
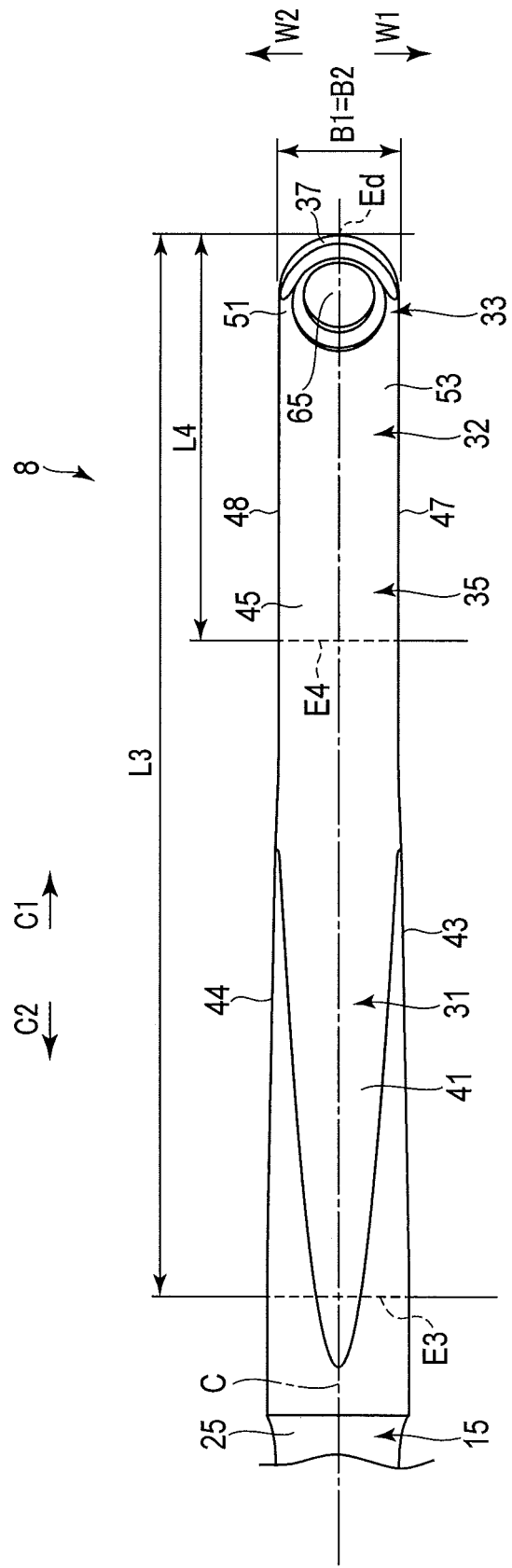
FIG. 14 is a schematic diagram in which the distal portion of the ultrasonic probe according to the second embodiment is seen from the second crossing direction side.

FIGS. 13 and 14 are diagrams showing a configuration of the distal portion of the ultrasonic probe 8. FIG. 13 is a diagram in which the ultrasonic probe 8 is seen from one side (e.g. an arrow W1 side) of the width direction, and FIG. 14 is a diagram in which the ultrasonic probe 8 is seen from the second crossing direction side (an arrow P2 side). In the present embodiment as well, as shown in FIG. 13 and FIG. 14, the ultrasonic probe 8 includes the probe main body 15, the narrowed portion 31, the bent extending portions 32 and 33, and the intermediate extending portion 35. Additionally, in the present embodiment as well as in the first embodiment, the ultrasonic probe 8 includes the narrowed outer surfaces 41 to 44, the intermediate outer surfaces 45 to 48, the bent outer surfaces 51 to 54, and the distal outer surface 37, and the distal end Ed and the positions E1 to E8 are defined. Further, as in the first embodiment, the dimensions L1 to L6, T1 to T4, B1, B2, the minimum inside diameter φ0 of the sheath 7, the outside diameter φ1, the bending angles α1 and α2, and the bending radii R1 and R2 are defined, and in a certain example, each of these dimensions has the value described above in the first embodiment. Moreover, in the present embodiment as well, the curved surfaces 55 to 58 are provided in the ultrasonic probe 8, and in a certain example, each of the bending radius R3 of the curved surface 55 and the bending radius R4 of the curved surface 56 has the value described above in the first embodiment. In this example, however, each of the bending radius R5 of the curved surface 57 and the bending radius R6 of the curved surface 58 is 0.3 mm, in contrast to that in the example described above in the first embodiment. Further, in the present embodiment as well, each of the curved surfaces 55 and 56 extends in a range indicated by a broken line J1 in FIG. 13, and each of the curved surfaces 57 and 58 extends in a range indicated by a broken line J2 in FIG. 13.

FIG. 15 to FIG. 17 are diagrams showing a configuration of the second bent extending portion 33. FIG. 15 shows a state seen from the side of the first bent outer surface 51 (the second crossing direction side) in the thickness direction. FIG. 16 shows a state seen from the side of the second bent outer surface 52 (the first crossing direction side) in the thickness direction. FIG. 17 shows a section of the second bent extending portion 33 perpendicular to the width direction at the substantially middle position of the second bent extending portion in the width direction. As shown in FIG. 15 to FIG. 17, the distal outer surface 37 of the second bent extending portion 33 includes the distal curved surface 61 having the bending radius R7, and in a certain example, the bending radius R7 has the value described above in the first embodiment.

Furthermore, in the present embodiment as well, the inclined surface 62 is formed between the distal curved surface 61 and the first bent outer surface 51, and the inclined surface (first inclined surface) 62 extends in such a state as to incline with respect to the thickness direction of the second bent extending portion 33 and incline with respect to the first bent outer surface 51 (the extending direction of the second bent extending portion 33). In a certain example, the inclination angle α3 of the inclined surface 62 with respect to the first bent outer surface 51 has the value (45°) described above in the first embodiment. In the present embodiment, however, an inclined surface (second inclined surface) 64 is formed instead of the intermediate curved surface 63 between the distal curved surface 61 and the second bent outer surface 52. The inclined surface 64 extends in such a state as to incline with respect to the thickness direction of the second bent extending portion 33 and incline with respect to the second bent outer surface 52 (the extending direction of the second bent extending portion 33). In a certain example, an inclination angle α4 of the inclined surface 64 with respect to the second bent outer surface 52 is 45°.

Furthermore, in the present embodiment as well, the through-hole 65 is formed in the second bent extending portion 33, and the through-hole 65 has the hole central axis M and the hole defining surface 66. Moreover, the through-hole 65 has the opening (first opening) 67 which is open in the first bent outer surface 51, and the opening (second opening) 68 which is open in the second bent outer surface 52. In a certain example, the dimension L7 from the hole central axis M of the through-hole 65 up to the distal end Ed of the second bent extending portion 33 (the ultrasonic probe 8) in the extending direction of the second bent extending portion 33 has the value described above in the first embodiment.

In the present embodiment as well, the abrading blade (first abrading blade) 71 is formed as the blade portion at the boundary between the hole defining surface 66 and the inclined surface 62 in the first bent outer surface 51. Therefore, as in the first embodiment, in the first bent outer surface 51, the abrading blade 71 is formed in a part of the opening edge of the opening (first opening) 67 of the through-hole 65. In the present embodiment as well, the abrading blade 71 is formed into a substantially arc shape around the hole central axis M, and formed over the predetermined angular range around the hole central axis M in a part located on the distal side with respect to the hole central axis M.

Furthermore, in the second bent outer surface 52 according to the present embodiment, a part of the hole defining surface 66 is continuous with the inclined surface 64 at an opening edge of the opening (second opening) 68 of the through-hole 65. Further, an abrading blade (second abrading blade) 72 is formed as a blade portion at a boundary between the hole defining surface 66 and the inclined surface 64. Therefore, in the second bent outer surface 52, the abrading blade 72 is formed in a part of the opening edge of the opening 68 of the through-hole 65. The abrading blade 72 is formed as described above, and is therefore formed into a substantially arc shape around the hole central axis M. Further, the abrading blade 72 is formed over a predetermined angular range around the hole central axis M in a part located on the distal side with respect to the hole central axis M.

Moreover, in the present embodiment, the through-hole 65 has a circular-column-shaped portion 81 and truncated-cone-shaped portions 82 and 83. Herein, in the through-hole 65, there are defined a boundary position Q2 between the circular-column-shaped portion 81 and the truncated-cone-shaped portion (first truncated-cone-shaped portion) 82, and a boundary position Q3 between the circular-column-shaped portion 81 and the truncated-cone-shaped portion (second truncated-cone-shaped portion) 83. The circular-column-shaped portion 81 extends along the thickness direction of the second bent extending portion 33 between the boundary position (first boundary position) Q2 and the boundary position (second boundary position) Q3. The circular-column-shaped portion 81 is located apart from the bent outer surfaces 51 and 52 in the thickness direction of the second bent extending portion 33. In the circular-column-shaped portion 81, the sectional area of the through-hole 65 perpendicular to the extending direction of the through-hole 65 is substantially uniform over the entire, length in the extending direction (the direction along the hole central axis M) of the through-hole 65. In a certain example, a diameter ϕ4 of the through-hole 65 in the circular-column-shaped portion 81 is 1.6 to 2 mm.

The truncated-cone-shaped portion (first truncated-cone-shaped portion) 82 extends from the boundary position Q2 up to the abrading blade (first abrading blade) 71 formed on the opening edge of the opening (first opening) 67 in the extending direction of the through-hole 65. In the truncated-cone-shaped portion 82, the sectional area of the through-hole 65 perpendicular to the extending direction of the through-hole 65 increases toward the abrading blade 71 (the first bent outer surface 51 side). For instance, in an example in which the diameter ϕ4 of the through-hole 65 in the circular-column-shaped portion 81 (i.e. the boundary position Q2) is 2 mm, a diameter ϕ5 of the through-hole 65 in the abrading blade 71 increases to 2.5 mm, and in an example in which the diameter ϕ4 of the through-hole 65 is 1.6 mm, the diameter ϕ5 of the through-hole 65 in the abrading blade 71 increases to 2.1 mm. Moreover, in this example, an opening angle (first opening angle) α5 of the truncated-cone-shaped portion 82 is 60°.

The truncated-cone-shaped portion (second truncated-cone-shaped portion) 83 extends from the boundary position Q3 up to the abrading blade (second abrading blade) 72 formed on the opening edge of the opening (second opening) 68 in the extending direction of the through-hole 65. In the truncated-cone-shaped portion 83, the sectional area of the through-hole 65 perpendicular to the extending direction of the through-hole 65 increases toward the abrading blade 72 (the second bent outer surface 52 side). For instance, in an example in which the diameter ϕ4 of the through-hole 65 in the circular-column-shaped portion 81 (i.e. the boundary position Q3) is 2 mm, a diameter ϕ6 of the through-hole 65 in the abrading blade 72 increases to 2.5 mm, and in an example in which the diameter ϕ4 of the through-hole 65 is 1.6 mm, the diameter ϕ6 of the through-hole 65 in the abrading blade 72 increases to 2.1 mm. Moreover, in this example, an opening angle (second opening angle) α6 of the truncated-cone-shaped portion 83 is 60°.

Figure 18:
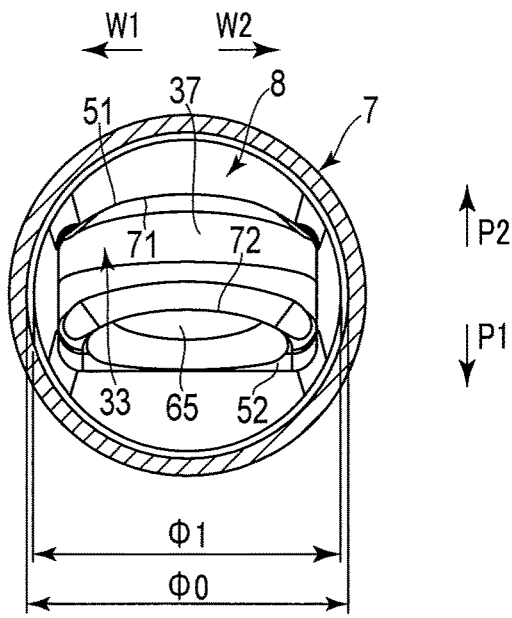
FIG. 18 is a schematic diagram in which the sheath and the ultrasonic probe according to the second embodiment are seen from the distal side.

FIG. 18 is a diagram in which the sheath 7 and the ultrasonic probe 8 are seen from the distal side. As shown in FIG. 18, in the present embodiment as well, in the projection seen from the distal side, the narrowed portion 31, the first bent extending portion 32, the second bent extending portion 33, and the intermediate extending portion 35 are located within the minimum inside diameter ϕ0 of the sheath 7. Further, in the present embodiment as well, in the projection seen from the distal side, the narrowed portion 31, the first bent extending portion 32, the second bent extending portion 33, and the intermediate extending portion 35 are located within the outside diameter ϕ1 of the ultrasonic probe 8 at the boundary position E1.

In the present embodiment as well, functions and advantageous effects similar to those in the first embodiment are provided.

Figure 19:
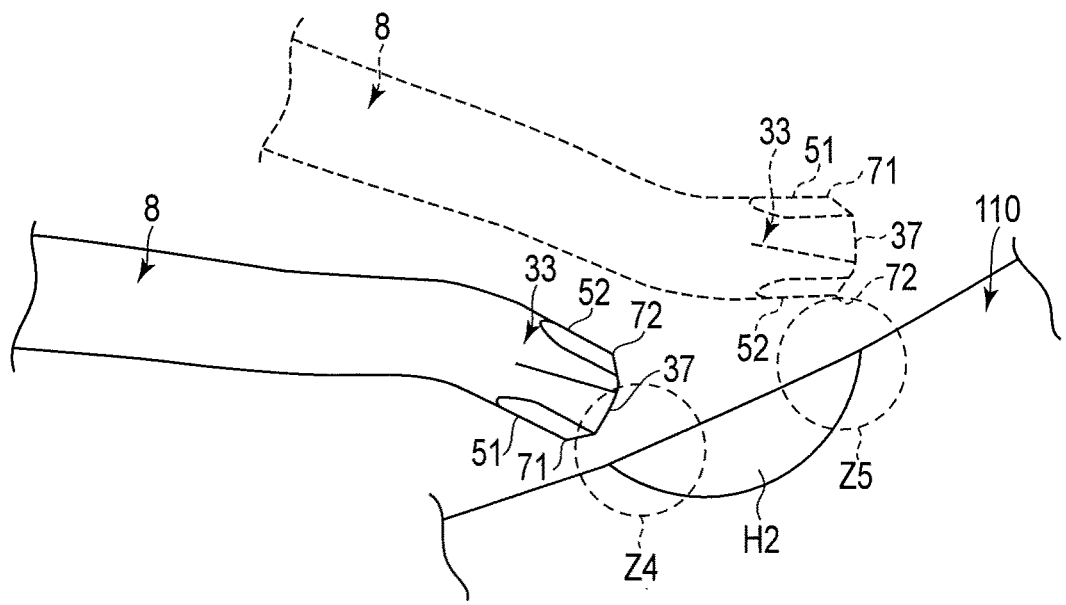
FIG. 19 is a schematic diagram showing one example of a treatment in which the treated target is abraded by use of the ultrasonic probe including two abrading blades according to the second embodiment.

Furthermore, FIG. 19 is a diagram showing one example of a treatment in which the treated target is abraded by use of the ultrasonic probe 8 including the two abrading blades 71 and 72. In FIG. 19, an affected part H2 of a bone 110 is abraded as a treated target by use of the ultrasonic probe 8. Herein, the abrading blade (first abrading blade) 71 provided in the first bent outer surface 51 is easily brought into contact with a zone Z4 of the treated target (H2), and the abrading blade (second abrading blade) 72 provided in the second bent outer surface 52 is easily brought into contact with a zone Z5 of the treated target (H2). Therefore, the surgeon abrades the zone Z4 of the treated target (H2) by use of the abrading blade 71, and abrades the zone Z5 of the treated target (H2) by use of the abrading blade 72. In the present embodiment, the abrading blade (corresponding one of 71 and 72) is provided in each of the first bent outer surface 51 and the second bent outer surface 52, so that both of the zones Z4 and Z5 can be abraded with one ultrasonic probe 8 (ultrasonic treatment instrument 2) alone. That is, it is possible to abrade both of the zones Z4 and Z5 without replacing the ultrasonic treatment instrument 2 (i.e., without pulling the ultrasonic probe 8 inserted in the articular cavity out of the body). This improves treatability in the treatment in which the treated target (H2) is abraded.

Modification

In the embodiment and others described above, the ultrasonic probe (8) used for surgery in a joint includes the probe main body (15) which extends from the proximal side toward the distal side along the linear longitudinal axis (C) and with which the ultrasonic transducer (12) generating ultrasonic vibration is connected on the proximal side, and the narrowed portion (31) which is continuous with the distal side of the probe main body (15) and whose sectional area perpendicular to the longitudinal axis (C) decreases from the proximal side toward the distal side. The ultrasonic probe (8) includes the first bent extending portion (32) which is provided on the distal side with respect to the narrowed portion (31) and which extends in such a state as to bend toward the first crossing direction (P1) side with respect to the longitudinal axis (C) when the first crossing direction (P1) crossing the longitudinal axis (C) is defined, and the second bent extending portion (33) which is continuous with the distal side of the first bent extending portion (32) and which extends in such a state as to bend toward the second crossing direction (P2) side with respect to the longitudinal axis (C) when the second crossing direction (P2) opposite to the first crossing direction (P1) is defined. The second bent extending portion (33) includes the blade portion (71; 71, 72) with which a bone or a cartilage is abraded in the joint by use of the ultrasonic vibration. In a projection seen from the distal side, the narrowed portion (31), the first bent extending portion (32), and the second bent extending portion (33) are located within the minimum inside diameter ($\phi 0$) of the sheath (7) through which the ultrasonic probe (8) is inserted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe which is used for surgery in a joint and which transmits ultrasonic vibration from a proximal side to a distal side, the ultrasonic probe comprising:
   a probe main body which extends along a linear longitudinal axis from the proximal side toward the distal side and to which an ultrasonic transducer generating the ultrasonic vibration is connected on the proximal side;
   a narrowed portion which is continuous with the distal side of the probe main body and whose sectional area in a section perpendicular to the longitudinal axis decreases from the proximal side toward the distal side;
   a first bent extending portion which is provided on the distal side with respect to the narrowed portion and which extends in such a state as to bend toward a first crossing direction side with respect to the longitudinal axis when the first crossing direction crossing the longitudinal axis is defined;
   a second bent extending portion which is continuous with the distal side of the first bent extending portion and which extends in such a state as to bend toward a second crossing direction side with respect to the longitudinal axis when the second crossing direction opposite to the first crossing direction is defined;
   a first bent outer surface facing toward the second crossing direction side in an outer surface of the second bent extending portion; and
   a first blade portion provided on the first bent outer surface of the second bent extending portion and with which a bone or a cartilage is abraded in the joint by use of the ultrasonic vibration,
   wherein:
      in a projection seen from the distal side, the narrowed portion, the first bent extending portion, and the second bent extending portion are located within a minimum inside diameter of a sheath through which the ultrasonic probe is inserted;
      the second bent extending portion includes a second bent outer surface facing toward the first crossing direction side in the outer surface, and a second blade portion provided in the second bent outer surface;
      the second bent extending portion has a through-hole pierced in the second bent extending portion from the first bent outer surface up to the second bent outer surface;
      the first blade portion is formed on an opening edge of the through-hole in the first bent outer surface; and
      the through-hole has a truncated-cone shape extending up to the first blade portion in a state where a sectional area of the through-hole perpendicular to an extending direction of the through hole increases toward the first blade portion.

2. An ultrasonic probe which is used for surgery in a joint and which transmits ultrasonic vibration from a proximal side to a distal side, the ultrasonic probe comprising:
   a probe main body which extends along a linear longitudinal axis from the proximal side toward the distal side and to which an ultrasonic transducer generating the ultrasonic vibration is connected on the proximal side;
   a narrowed portion which is continuous with the distal side of the probe main body and whose sectional area in a section perpendicular to the longitudinal axis decreases from the proximal side toward the distal side;
   a first bent extending portion which is provided on the distal side with respect to the narrowed portion and which extends in such a state as to bend toward a first crossing direction side with respect to the longitudinal axis when the first crossing direction crossing the longitudinal axis is defined;
   a second bent extending portion which is continuous with the distal side of the first bent extending portion and which extends in such a state as to bend toward a second crossing direction side with respect to the longitudinal axis when the second crossing direction opposite to the first crossing direction is defined;
   a first bent outer surface facing toward the second crossing direction side in an outer surface of the second bent extending portion; and
   a first blade portion provided on the first bent outer surface of the second bent extending portion and with which a bone or a cartilage is abraded in the joint by use of the ultrasonic vibration,
   wherein:
      in a projection seen from the distal side, the narrowed portion, the first bent extending portion, and the second bent extending portion are located within a minimum inside diameter of a sheath through which the ultrasonic probe is inserted;
      the second bent extending portion includes second bent outer surface facing toward the first crossing direction side in the outer surface, and a second blade portion provided in the second bent outer surface;
      the second bent extending portion has a through-hole pierced in the second bent extending portion from the first bent outer surface up to the second bent outer surface;
      the first blade portion is formed on an opening edge of the through-hole in the first bent outer surface; and
      the second blade portion is formed on an opening edge of the through-hole in the second bent outer surface.

3. The ultrasonic probe according to claim 2, wherein a dimension of the second bent extending portion in a thickness direction thereof from the first bent outer surface up to the second bent extending portion is 1.5 mm.

4. The ultrasonic probe according to claim 2, wherein the first bent extending portion includes
a third bent outer surface which faces toward the second crossing direction side and which is continuous with the proximal side of the first bent extending portion, and
a fourth bent outer surface which faces toward the first crossing direction side and which is continuous with the proximal side of the second bent extending portion.

5. The ultrasonic probe according to claim 2, wherein a dimension of
the first bent extending portion in a thickness direction thereof from the third bent outer surface up to the fourth bent outer surface is 1.5 mm.

6. The ultrasonic probe according to claim 2, wherein a dimension in
a direction along the longitudinal axis up to a distal end of the second bent extending portion from a boundary position between the second bent outer surface and the fourth bent outer surface is 2.35 mm.

7. The ultrasonic probe according to claim 2, further comprising an
intermediate outer surface which is continuous with the proximal side of the fourth bent outer surface and which extends along the longitudinal axis in such a state as to face toward the first crossing direction side, wherein a dimension in a direction along the longitudinal axis up to a distal end of the second bent extending portion from a boundary position between the fourth bent outer surface and the intermediate outer surface is 5 to 6.5 mm.

8. The ultrasonic probe according to claim 2, claim 1, wherein a bending angle of the first bent extending portion to the first crossing direction side with respect
to the longitudinal axis is 5°, and
a bending angle of the second bent extending portion to the second crossing direction side with respect to the longitudinal axis is 20°.

9. The ultrasonic probe according to claim 2, wherein in a projection seen from the distal side, the narrowed portion, the first bent extending portion, and the second bent extending portion are located within an outside diameter of the ultrasonic probe at a boundary position between the probe main body and the narrowed portion.

10. The ultrasonic probe according to claim 2, wherein the minimum inside diameter of the sheath through which the ultrasonic probe is inserted is 4 mm,
and
the outside diameter of the ultrasonic probe at the boundary position between the probe main body and the narrowed portion is 3.8 mm.

11. The ultrasonic probe according to claim 2, wherein the minimum
inside diameter of the sheath through which the ultrasonic probe is inserted is 3.4 mm, and the outside diameter of the ultrasonic probe at the boundary position between the probe main body and the narrowed portion is 2.9 mm.

12. An ultrasonic treatment instrument which perform surgery in a joint with using ultrasonic vibration, the ultrasonic treatment instrument comprising:
an ultrasonic transducer generating the ultrasonic vibration;
a probe main body which extends along a linear longitudinal axis from a proximal side toward a distal side and to which the ultrasonic transducer is connected on the proximal side, the probe main body transmitting the ultrasonic vibration from the proximal side to the distal side;
a narrowed portion which is continuous with the distal side of the probe main body and whose sectional area in a section perpendicular to the longitudinal axis decreases from the proximal side toward the distal side;
a first bent extending portion which is provided on the distal side with respect to the narrowed portion and which extends in such a state as to bend toward a first crossing direction side with respect to the longitudinal axis when the first crossing direction crossing the longitudinal axis is defined;
a second bent extending portion which is continuous with the distal side of the first bent extending portion and which extends in such a state as to bend toward a second crossing direction side with respect to the longitudinal axis when the second crossing direction opposite to the first crossing direction is defined;
a first bent outer surface facing toward the second crossing direction side in an outer surface of the second bent extending portion; and
a first blade portion provided on the first bent outer surface of the second bent extending portion and with which a bone or a cartilage is abraded in the joint by use of the ultrasonic vibration,
wherein:
in a projection seen from the distal side, the narrowed portion, the first bent extending portion, and the second bent extending portion are located within a minimum inside diameter of a sheath through which the ultrasonic probe is inserted;
the second bent extending portion includes second bent outer surface facing toward the first crossing direction side in the outer surface, and a second blade portion provided in the second bent outer surface;
the second bent extending portion has a through-hole pierced in the second bent extending portion from the first bent outer surface up to the second bent outer surface;
the first blade portion is formed on an opening edge of the through-hole in the first bent outer surface; and
the second blade portion is formed on an opening edge of the through-hole in the second bent outer surface.

13. The ultrasonic probe according to claim 2, wherein:
the second bent extending portion includes a hole defining surface and an inclined surface; and
the first blade portion is provided between the hole defining surface and the inclined surface.

14. The ultrasonic probe according to claim 2, wherein the through-hole has a first truncated-cone-shaped portion which extends up to the first blade portion in a state where a sectional area of the through-hole perpendicular to an extending direction of the through-hole increases toward the first blade portion, and a second truncated-cone-shaped portion which extends up to the second blade portion in a state where the sectional area of the through-hole perpendicular to the extending direction of the through-hole increases toward the second blade portion.

* * * * *